(12) United States Patent
Pascoguin et al.

(10) Patent No.: US 9,315,846 B2
(45) Date of Patent: Apr. 19, 2016

(54) FLUIDIC CHANNEL BASED ON A FILTERED, FREE-SPACE ELECTROMAGNETIC WAVE SOURCE

(71) Applicants: Bienvenido Melvin L. Pascoguin, La Mesa, CA (US); Ryan P. Lu, San Diego, CA (US); Ayax D. Ramirez, Chula Vista, CA (US)

(72) Inventors: Bienvenido Melvin L. Pascoguin, La Mesa, CA (US); Ryan P. Lu, San Diego, CA (US); Ayax D. Ramirez, Chula Vista, CA (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 319 days.

(21) Appl. No.: 14/179,658

(22) Filed: Feb. 13, 2014

(65) Prior Publication Data
US 2015/0226242 A1    Aug. 13, 2015

(51) Int. Cl.
| | | |
|---|---|---|
| C12Q 1/00 | (2006.01) | |
| G01N 30/00 | (2006.01) | |
| F15D 1/00 | (2006.01) | |
| G01N 35/00 | (2006.01) | |
| B01L 3/00 | (2006.01) | |
| G01N 35/10 | (2006.01) | |

(52) U.S. Cl.
CPC ............... *C12Q 1/00* (2013.01); *B01L 3/50273* (2013.01); *B01L 3/502784* (2013.01); *F15D 1/0075* (2013.01); *G01N 35/00* (2013.01); *B01L 2200/0673* (2013.01); *B01L 2300/166* (2013.01); *B01L 2400/0454* (2013.01); *G01N 2035/1046* (2013.01); *Y10T 137/2104* (2015.04)

(58) Field of Classification Search
CPC ...... G02B 21/32; G02B 5/0273; G02B 5/188; B01L 3/502761; G01N 15/1434; G01N 30/00; G03H 1/0005
USPC ......... 250/251, 216, 222.2, 573; 359/558, 15, 359/614, 641
See application file for complete search history.

(56) References Cited

U.S. PATENT DOCUMENTS

| | | | |
|---|---|---|---|
| 6,737,634 B2 * | 5/2004 | Curtis ................ | B01F 13/0052 250/222.2 |
| 6,995,351 B2 | 2/2006 | Curtis et al. | |
| 7,109,473 B2 | 9/2006 | Grier et al. | |
| 7,118,676 B2 * | 10/2006 | Mueth ..................... | A61M 1/36 210/729 |
| 7,150,834 B2 | 12/2006 | Mueth et al. | |

(Continued)

OTHER PUBLICATIONS

Sendhil Raja S. et al.; Bessel & Laguerre-Gauss Beam Generation Using SLM as a Reconfigurable Diffractive Optical Element; Science, available online at http://een.iust.ac.ir/profs/Sadr/Papers/intp3.pdf, accessed on Feb. 12, 2014.

(Continued)

*Primary Examiner* — David A Vanore
(74) *Attorney, Agent, or Firm* — Spawar Systems Center Pacific; Kyle Eppele; J. Eric Anderson (57) ABSTRACT

A fluid-channeling device comprising: a fluid source; and a beam generator configured to generate a collimated vortex beam, wherein the beam generator is operatively coupled to the fluid source such that fluid from the fluid source may be introduced into a vortex of the collimated vortex beam, and wherein the collimated vortex beam is tuned such that when the fluid is in the vortex the fluid interacts with the collimated vortex beam to create an insulating pseudo-wall between the collimated vortex beam and the fluid such that the fluid is suspended in, and capable of traveling through, the vortex.

20 Claims, 9 Drawing Sheets

38

- Generate a first optical beam. — 38$_a$
- Filter the first optical beam to create a collimated vortex beam having a radiation pressure greater than or equal to a vapor pressure of the first fluid, and wherein the temperature of the collimated vortex beam is greater than, or equal to, the Leidenfrost point of the first fluid. — 38$_b$
- Inject the first fluid into the vortex of the collimated vortex beam such that the first fluid is suspended within the vortex due to the Leidenfrost effect by a layer of first fluid vapor. — 38$_c$
- Drive the first fluid through the vortex along the path of the collimated vortex beam by pumping a pulse of gas along the propagation path of the collimated vortex beam. — 38$_d$

(56) References Cited

U.S. PATENT DOCUMENTS

| | | | |
|---|---|---|---|
| 7,444,817 B2 * | 11/2008 | Ito | G02B 21/32 60/650 |
| 7,482,577 B2 | 1/2009 | Gruber et al. | |
| 7,491,928 B2 * | 2/2009 | Roichman | G02B 21/32 250/216 |
| 8,368,008 B2 * | 2/2013 | Schonbrun | G02B 21/32 250/251 |
| 8,502,148 B2 * | 8/2013 | Wagner | C12N 5/0612 250/338.1 |
| 8,637,803 B2 * | 1/2014 | Montes Usategu | G02B 21/32 250/216 |
| 8,767,135 B2 * | 7/2014 | Hikmet | A47F 11/10 349/34 |
| 8,829,426 B2 * | 9/2014 | Vertes | H01J 49/0404 250/282 |
| 2003/0066956 A1 | 4/2003 | Gruber et al. | |
| 2004/0021949 A1 * | 2/2004 | Grier | C12N 13/00 359/614 |
| 2004/0067167 A1 * | 4/2004 | Zhang | G01N 15/147 422/82.05 |
| 2009/0032449 A1 * | 2/2009 | Mueth | G02B 21/32 210/94 |
| 2010/0204459 A1 * | 8/2010 | Mason | B01J 13/0004 530/408 |
| 2015/0338324 A1 * | 11/2015 | Gigan | B01L 3/502761 435/5 |
| 2015/0377764 A1 * | 12/2015 | Pan | G01N 15/1463 356/36 |

OTHER PUBLICATIONS

Galvez et al.; Composite Optical Vortices Formed by Collinear Laguerre-Gauss Beams; Proc. SPIE 6131, Nanomanipulation with Light II, 613105, Feb. 9, 2006.

Kotlyar et al.; Diffraction of a Finite-Radius Plane Wave and a Gaussian Beam by a Helical Axicon and a Spiral Phase Plate; Optical Society of America; vol. 24, No. 7, Jul. 2007.

Wang et al.; Dynamic Switching of Optical Vortices with Dynamic Gamma-Correction Liquid Crystal Spiral Phase Plate; Optices Express, vol. 13, No. 25; Dec. 12, 2005.

Karimi et al.; Hypergeometric-Gaussian Modes; Optics Letters, vol. 32, No. 21, Nov. 1, 2007.

Lukin et al.; Beam Spreading of Vortex Beams Propagating in Turbulent Atmosphere; Applied Optics, vol. 51, No. 10, Apr. 1, 2012.

J. Arlt et al.; Generation of a Beam with a Dark Focus Surrounded by Regions of Higher Intensity: the Optical Bottle Beam; Optics Letters, vol. 25, No. 4; Feb. 15, 2000.

Pascoguin et al.; Complete Optical Encapsulation of Particulates; Unpublished U.S. Appl. No. 13/532,372, filed Jun. 25, 2012.

* cited by examiner

FLUIDIC CHANNEL BASED ON A FILTERED, FREE-SPACE ELECTROMAGNETIC WAVE SOURCE

FEDERALLY-SPONSORED RESEARCH AND DEVELOPMENT

The United States Government has ownership rights in this invention. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 101440.

BACKGROUND OF THE INVENTION

The current invention relates to the field of fluid transport. In the past others have used many different means to transport fluid from one location to another. Typically such means employ some form of solid-walled channel, tube, and/or pipe to conduct the fluid from one point "A" to point "B". A need exists for alternative means for transporting fluid from one location to another.

SUMMARY

Disclosed herein is a fluid-channeling device comprising a fluid source and a beam generator. The beam generator is configured to generate a collimated vortex beam, and the beam generator is operatively coupled to the fluid source such that fluid from the fluid source may be introduced into a vortex of the collimated vortex beam. The collimated vortex beam is tuned such that when the fluid is in the vortex the fluid interacts with the collimated vortex beam to create an insulating pseudo-wall between the collimated vortex beam and the fluid such that the fluid is suspended in, and capable of traveling through, the vortex.

The fluid-channeling device disclosed herein may be used to transport a fluid according to the following steps. The first step provides for generating a first optical beam. The second step provides for filtering the first optical beam to create a collimated vortex beam having a radiation pressure greater than or equal to a vapor pressure of the first fluid. The temperature of the collimated vortex beam is greater than, or equal to, the Leidenfrost point of the fluid. The next step provides for injecting the first fluid into the vortex of the collimated vortex beam such that the first fluid is suspended within the vortex due to the Leidenfrost effect by a layer of fluid vapor/gas. The next step provides for driving the fluid through the vortex along the path of the collimated vortex beam by pumping a pulse of gas along the propagation path of the collimated vortex beam.

An embodiment of the fluid-channeling device may be described as a microfluidic-channeling device comprising a beam generator, a filter, a fluid injector, and a fluid receiver. The beam generator is configured to output a first optical beam. The filter is configured to transform the first optical beam into a collimated vortex beam. The fluid injector is configured to inject a fluid into the vortex of the collimated vortex beam. The temperature of the collimated vortex beam is greater than, or equal to, the Leidenfrost point of the fluid. The collimated vortex beam has a radiation pressure greater than or equal to a vapor pressure of the fluid, such that the fluid is held within, and is capable of moving through, the vortex due to the Leidenfrost effect. The fluid receiver is optically aligned with the collimated vortex beam and configured to receive the fluid from the vortex.

BRIEF DESCRIPTION OF THE DRAWINGS

Throughout the several views, like elements are referenced using like references. The elements in the figures are not drawn to scale and some dimensions are exaggerated for clarity.

DETAILED DESCRIPTION OF EMBODIMENTS

Figure 1A:
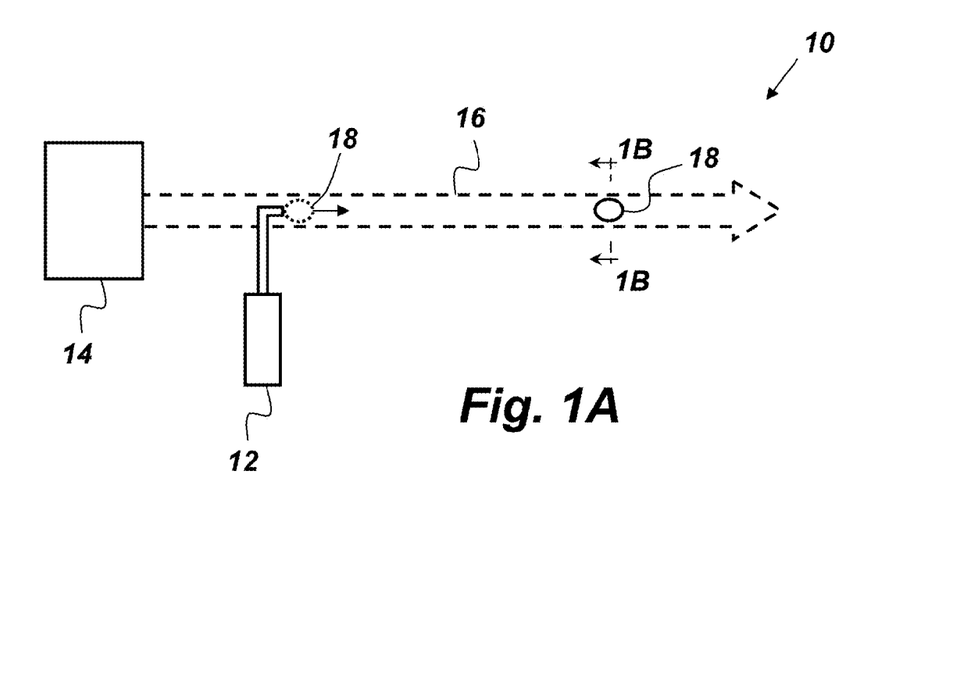
FIG. 1A is a side-view illustration of an embodiment of a fluid-channeling device.
Figure 1B:
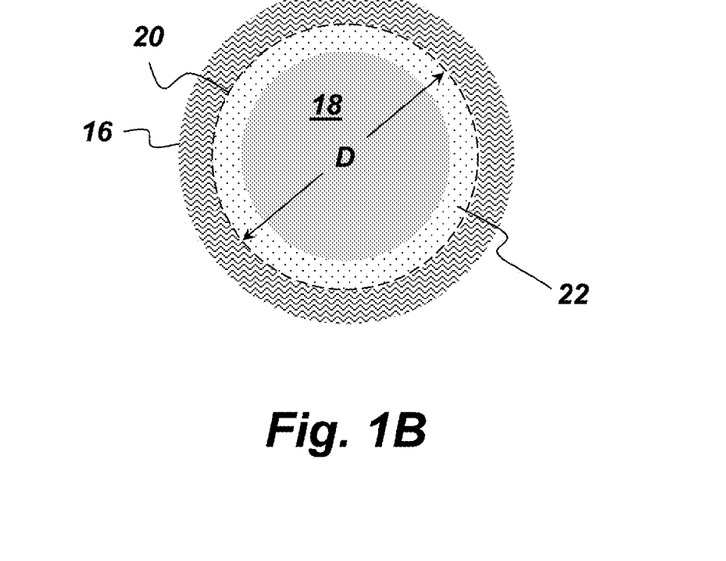
FIG. 1B is a cross-sectional view of a collimated vortex beam.

FIG. 1A depicts an embodiment of a fluid-channeling device 10 comprising, consisting of, or consisting essentially of a fluid source 12 and a beam generator 14. The beam generator 14 may be configured to generate a collimated vortex beam 16. The beam generator 14 may be operatively coupled to the fluid source 12 such that fluid 18 from the fluid source 12 may be introduced into a vortex 20 of the collimated vortex beam 16. FIG. 1B is a cross-sectional view of the collimated vortex beam 16 with fluid 18 inside the vortex 20. In FIG. 1B, the vortex 20 is depicted as the area within the dotted line. The collimated vortex beam 16 may be tuned such that when the fluid 18 is in the vortex 20 the fluid 18 interacts with the collimated vortex beam 16 to create an insulating pseudo-wall 22 between the collimated vortex beam 16 and the fluid 18 such that the fluid 18 is suspended in, and capable of traveling through, the vortex 20.

The beam generator 14 may be any optical beam source capable of creating the collimated vortex beam 16. The collimated vortex beam 16 may be any beam with a hollow interior such as an nth ordered-Bessel beam or a Laguerre-Gaussian (LG) beam. The fluid 18 may be any liquid, plasma, and/or a gas. The beam generator 14 and the fluid 18 may be matched such that the electromagnetic (EM) wave skin depth of the fluid 18 is less than the diameter D of the vortex 20. The skin depth is a measure of how much energy absorption the fluid 18 will have as a function of the wavelength of the collimated vortex beam 16. For example, the surface of a fluid exposed to an EM wave with a relatively long skin depth will not heat as quickly as the surface of a fluid having a relatively short skin depth. As an optical beam hits matter, the incident light intensity "$I_0$" decays exponentially. The light intensity "I" at a given depth of matter penetration x is given by $I=I_0 e^{x/c}$. Where C is a constant and x is the depth of matter penetration. The constant C for different materials is wavelength dependent. Thus, by changing the wavelength of the collimated vortex beam 16, the absorption of light in the fluid 18 will change and untimely change the thickness of the pseudo wall 22.

Figure 2:
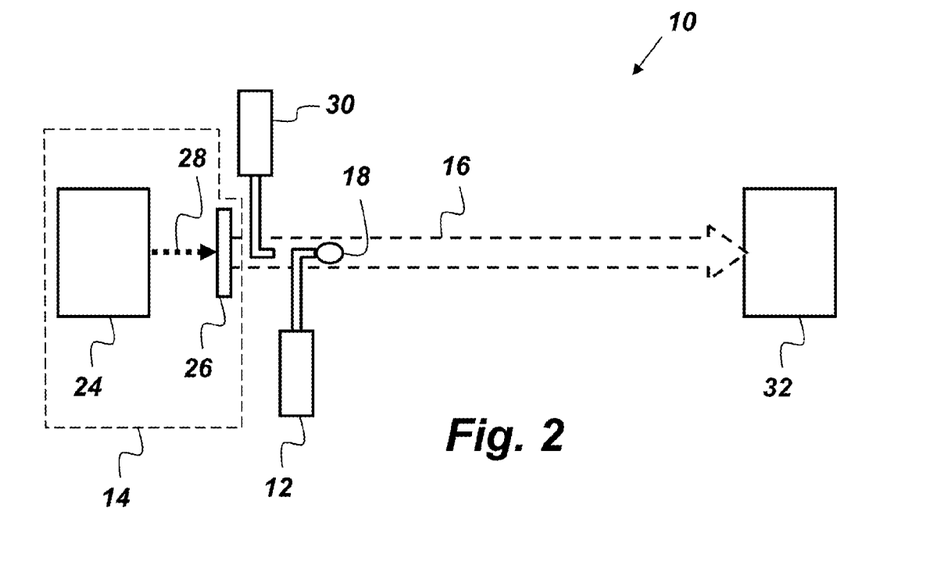
FIG. 2 is a side-view illustration of an embodiment of a fluid-channeling device.

FIG. 2 depicts an embodiment of the beam generator 14 that comprises a laser 24 and a spatial light modulator (SLM) filter 26. The laser 24 generates a laser beam 28. The SLM filter 26 is configured to transform the laser beam 28 into the collimated vortex beam 16. The SLM filter 26 may be encoded with phase only information and may optionally include amplitude information. Suitable examples of the SLM filter 26 include, but are not limited to, spiral phase plates, and filters that create hypergeometric-Gaussian modes, etcetera.

Figure 3:
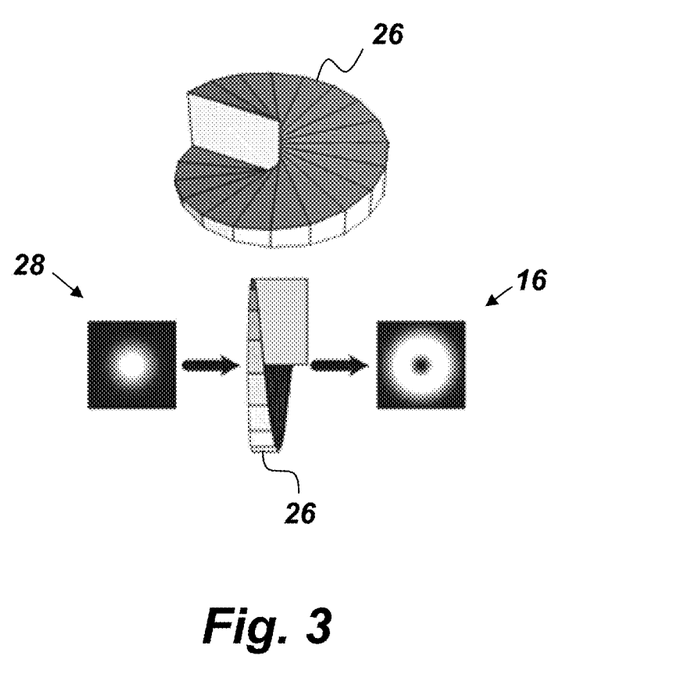
FIG. 3 is an illustration of a spatial light modulator filter.

FIG. 3 is an illustration schematically showing an example SLM filter 26 that may be used to transform a fundamental transverse mode of the laser beam 28 into a hollow cylindrical laser tube, i.e., the collimated vortex beam 16. Transverse electromagnetic (TEM) modes are may be defined as modes where neither electric nor magnetic fields are present in the direction of propagation. The fluid-channeling device 10 may utilize pulse or continuous lasers of various wavelengths which are compatible with the SLM filter 26 and the skin depth of the types of fluids 18.

Referring back to FIG. 2, once the fluid 18 is injected into the vortex 20 of the collimated vortex beam 16, a fluid driver 30 may act upon the fluid 18 such that the fluid 18 travels through the vortex 20 until it arrives at a fluid receiver 32. The fluid driver 30 may be any means of causing the fluid 18 to travel through the vortex 20. One suitable example of the fluid driver 30 is a gas pulse generator (such as a source of compressed air) that is configured to generate a pulse of gas that pushes the fluid 18 through vortex 20. Another suitable example of the fluid driver 30 is a fan. For example, the fluid driver 30 may be an air filtration system that induces the air surrounding the fluid channeling device 10 to travel generally in a direction from the fluid source 12 toward the fluid receiver 32.

Figure 4A:
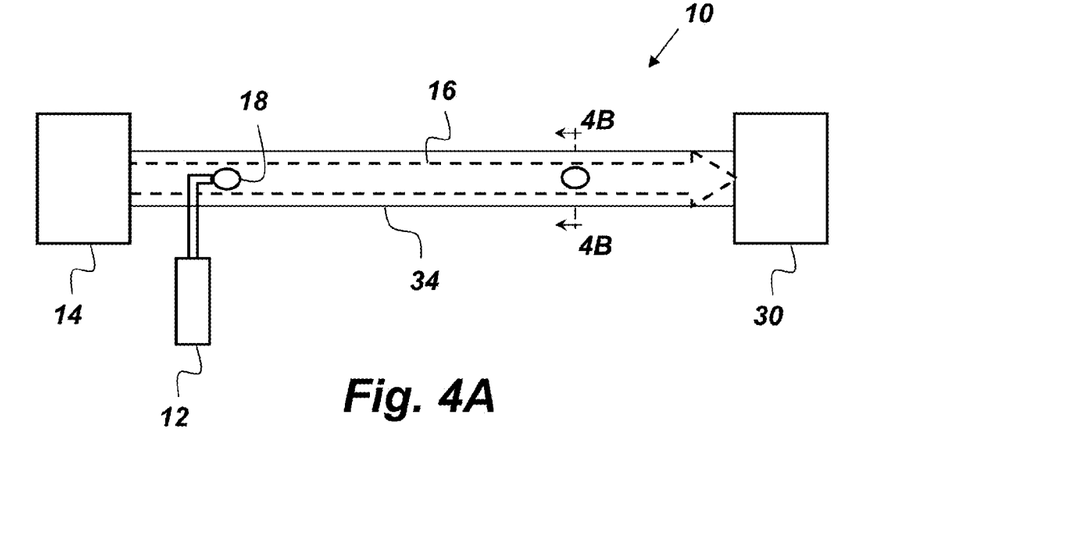
FIG. 4A is a side-view illustration of an embodiment of a fluid-channeling device.
Figure 4B:
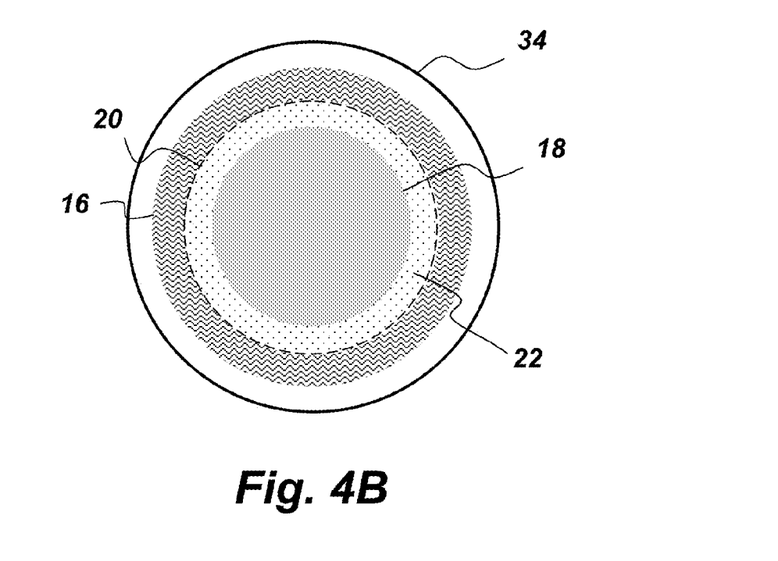
FIG. 4B is a cross-sectional view of a collimated vortex beam.

FIG. 4A is an illustration of an embodiment of the fluid-channeling device 10 comprising a tubular enclosure 34 configured to surround the vortex beam 16 between the fluid driver 30 and the fluid source 12 without touching the vortex beam 16. In this embodiment, the fluid driver 30 is a suction pump configured to pull the fluid 18 through the vortex 20. FIG. 4B is a cross-sectional view of the tubular enclosure 34, the collimated vortex beam 16, and the fluid 18 within the vortex 20.

In embodiments of the fluid-channeling device 10 where the fluid 18 is a liquid, the collimated vortex beam 16 may be used to suspend the liquid inside the vortex 20 due to the Leidenfrost effect. The Leidenfrost effect may be utilized to generate the pseudo wall 22 by rapidly boiling the liquid to create a wall of vapor/gas of some thickness that will vary as a function of the skin depth of the liquid and the wavelength of the collimated vortex beam 16. Provided that the temperature of the collimated vortex beam 16 is greater than the Leidenfrost point of the liquid and that the radiation pressure of the collimated vortex beam 16 is greater than or equal to the vapor pressure of the liquid, once the liquid is injected into the vortex 20 the liquid will be quickly surrounded, and held within the vortex 20, by the pseudo wall 22 without any support other than the collimated vortex beam 16 itself.

Referring still to the embodiment of the fluid-channeling device where the fluid 18 is a liquid, the pseudo wall 22 is analogous to a superhydrophobic surface with respect to the liquid. This is due to the fact that the liquid droplet is surrounded by a layer of vapor (i.e., the pseudo wall 22) that was created when the collimated vortex beam 16—having a temperature above the Leidenforst point—vaporized the outer surface of the droplet. The thickness of the pseudo wall 22 can be controlled by fine tuning the wavelength of the laser and/or doping the liquid to change the skin depth of the liquid. An external force, such as a pulse of air, applied to the liquid droplet inside the collimated vortex beam 16 causes the fluid 18 to move within the vortex 20 along the propagation path of the collimated vortex beam 16. This external force will create a single direction fluid flow on the superhydrophobic-like pseudo wall 22 inside the vortex 20. The vapor pressure of the pseudo wall 22 should balance against the radiation pressure of the collimated vortex beam 16 for the fluid 18 to remain within the confines of the vortex 20. In embodiments of the fluid-channeling device 10 where the fluid 18 is a gas, the gas may be held within the vortex due to a thin-film effect due to the reaction of the gas with the inner wall of the collimated vortex beam 16.

Figure 5A:
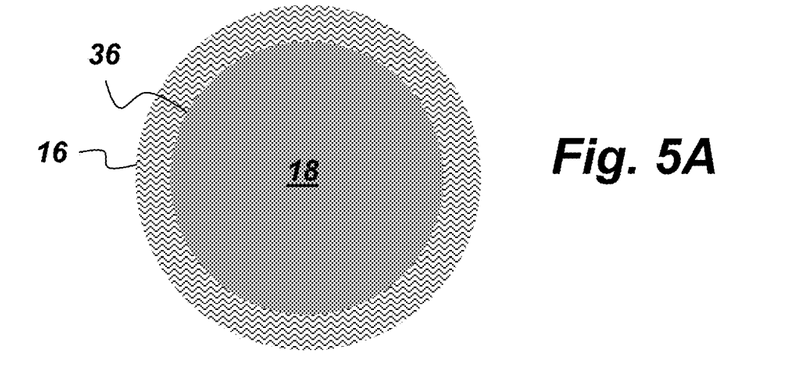
FIG. 5A is a cross-sectional view of a collimated vortex beam.
Figure 5B:
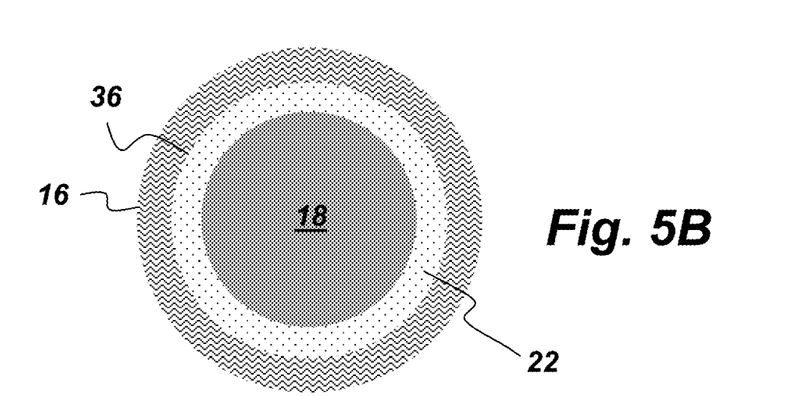
FIG. 5B is a cross-sectional view of a collimated vortex beam.
Figure 5C:
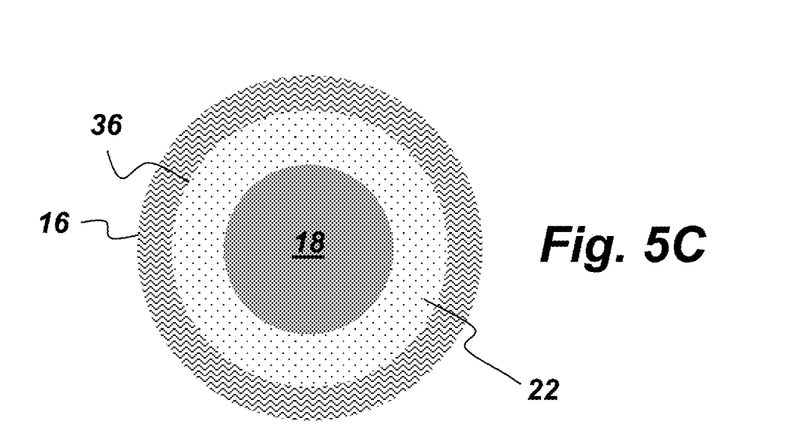
FIG. 5C is a cross-sectional view of a collimated vortex beam.

FIGS. 5A, 5B, and 5C show the gradual difference of the pseudo wall 22, or gradient layer, and the fluid 18 over time. When the fluid 18 is first introduced into the vortex 20, the fluid 18 comes into direct contact with an inner edge 36 of the collimated vortex beam 16, and, if the fluid 18 is a liquid, the pseudo wall 22 is immediately generated from the gradient temperature of the liquid due to the Leidenfrost effect. The fluid 18 interacts with the collimated vortex beam 16 to create the pseudo wall 22, which insulates the fluid 18 and holds it suspended within the vortex 20, such as is shown in FIG. 5B. FIG. 5C shows how, over time, the pseudo wall 22 grows as more of the fluid 18 is transformed into the pseudo wall 22.

Figure 6:
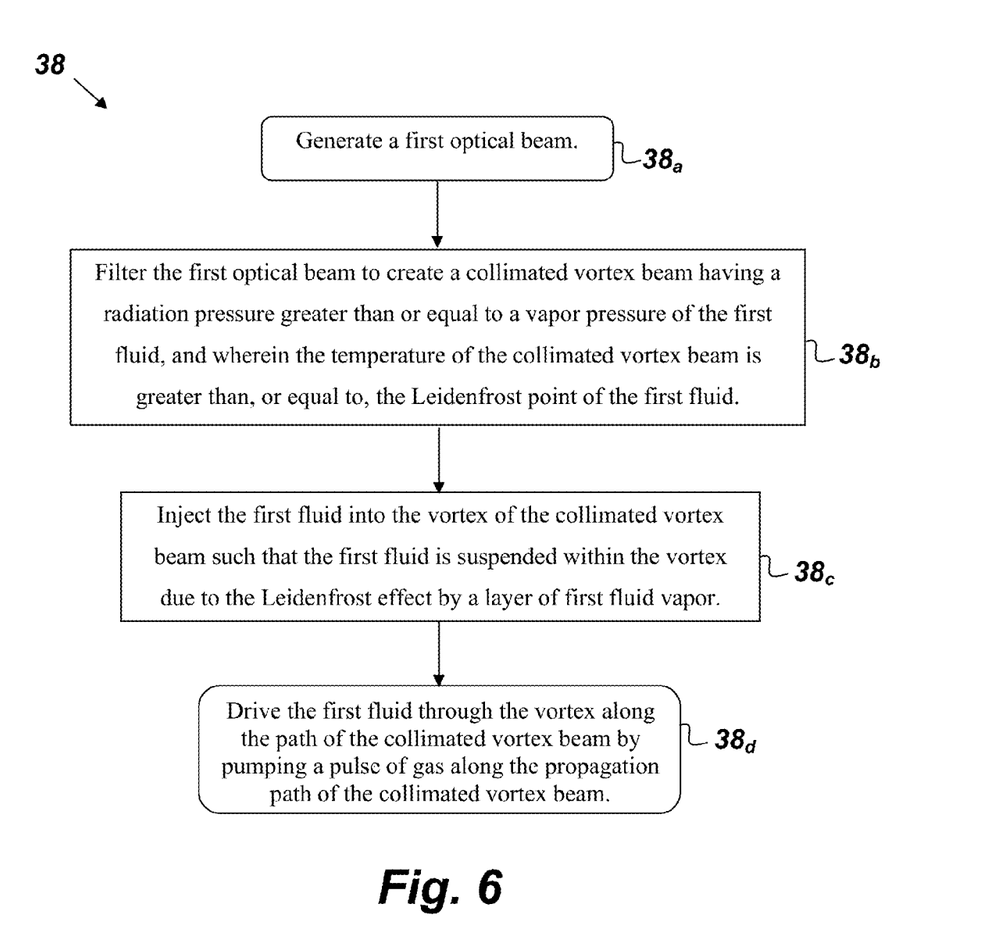
FIG. 6 is a flowchart of a method for using a fluid-channeling device.

FIG. 6 is a flowchart of a method 38 for using the fluid channeling device 10. The first step $38_a$ provides for generating a first optical beam. The second step $38_b$ provides for filtering the first optical beam to create a collimated vortex beam having a radiation pressure greater than or equal to a vapor pressure of the first fluid. The temperature of the collimated vortex beam should be greater than, or equal to, the Leidenfrost point of the first fluid such that the pseudo-wall is a layer of fluid vapor/gas created by the Leidenfrost effect. The next step $38_c$ provides for injecting the first fluid into the vortex of the collimated vortex beam such that the first fluid is suspended within the vortex due to the Leidenfrost effect by a layer of first fluid vapor. The next step $38_d$ provides for driving the first fluid through the vortex along the path of the collimated vortex beam by pumping a pulse of gas along the propagation path of the collimated vortex beam.

Figure 7:
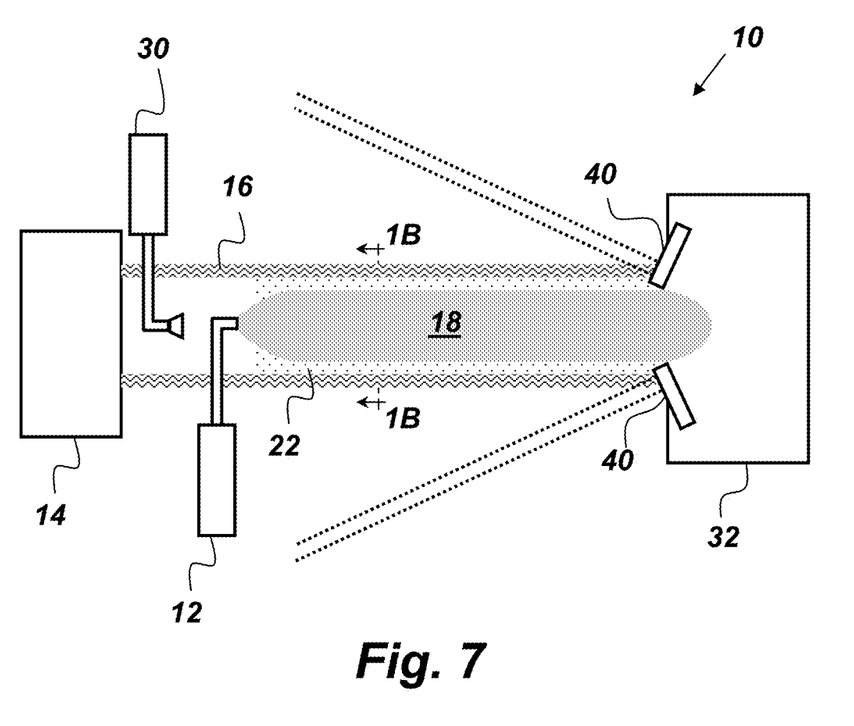
FIG. 7 is a side-view illustration of an embodiment of a fluid-channeling device.

FIG. 7 is a cross-sectional illustration of an embodiment of the fluid-channeling device 10. In this embodiment, the fluid 18 is transported through the vortex 20 and received at the fluid receiver 32, which comprises a mirror ring 40. The mirror ring 40 is configured to allow the fluid 18 to pass through the center of the mirror ring 40 into the receiver 32 while the mirror ring 40 deflects the collimated vortex beam 16 away from the receiver 32.

Figure 8:
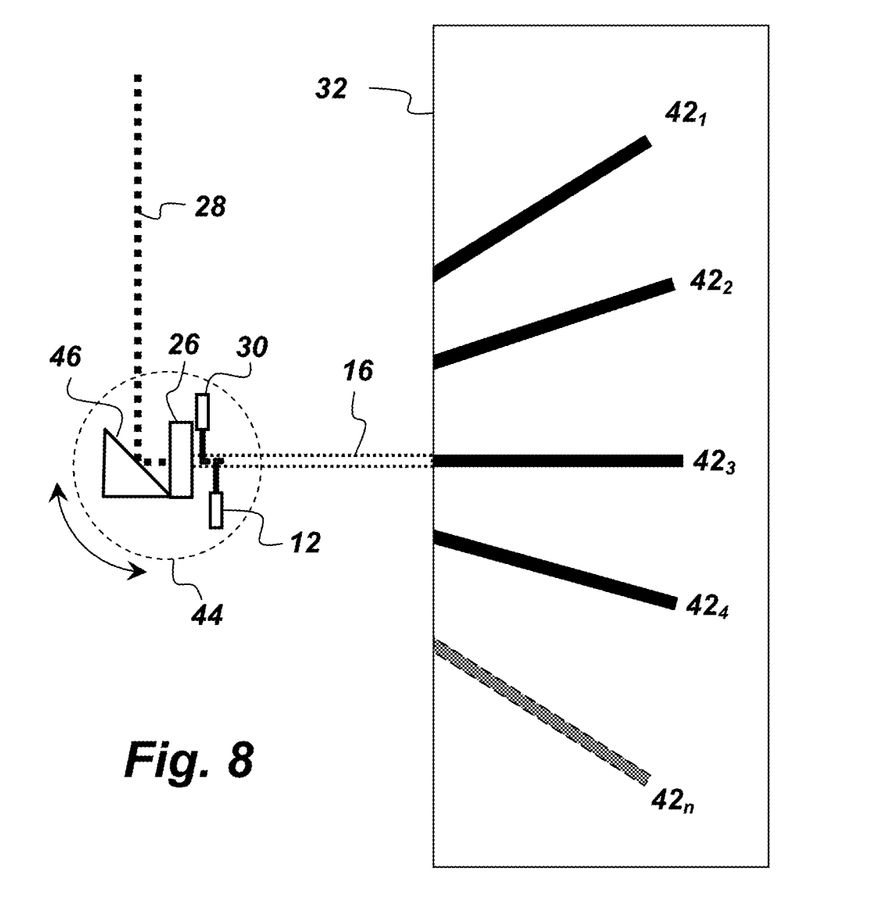
FIG. 8 is a side-view illustration of an embodiment of a fluid-channeling device.

FIG. 8 is an illustration of a multiplexer embodiment of the fluid-channeling device 10. In this embodiment, the fluid receiver 32 comprises multiple receiving channels $42_1$-$42_n$. In a non-limiting example embodiment, the receiving channels $42_1$-$42_n$ may be ports of a physical microfluidic platform configured for liquid payload delivery. The fluid 18 may be channeled into any one of the receiving channels $42_1$-$42_n$ by changing the propagation path of the collimated vortex beam 16 to align with the desired receiving channel 42. In the embodiment shown in FIG. 8, the changing of the propagation path of the collimated vortex beam 16 is accomplished by way of a rotatable assembly 44 comprising a mirror 46, the SLM filter 26, the fluid source 12, and the fluid driver 30. The mirror 46 is configured to redirect the incoming laser beam 28 to the SLM filter 26 where the laser beam is transformed into the collimated vortex beam 16. By rotating the rotatable assembly 44, the collimated vortex beam 16 may be aimed at any given receiving channel 42. Thus, fluid 18 may be transported from the fluid source 12 through free space to any given receiving channel 42. Any means for redirecting the collimated vortex beam 16 may be employed. Those having ordinary skill in the art will understand that there are many different ways to redirect the collimated vortex beam 16 in addition to the embodiment described above.

Figure 9:
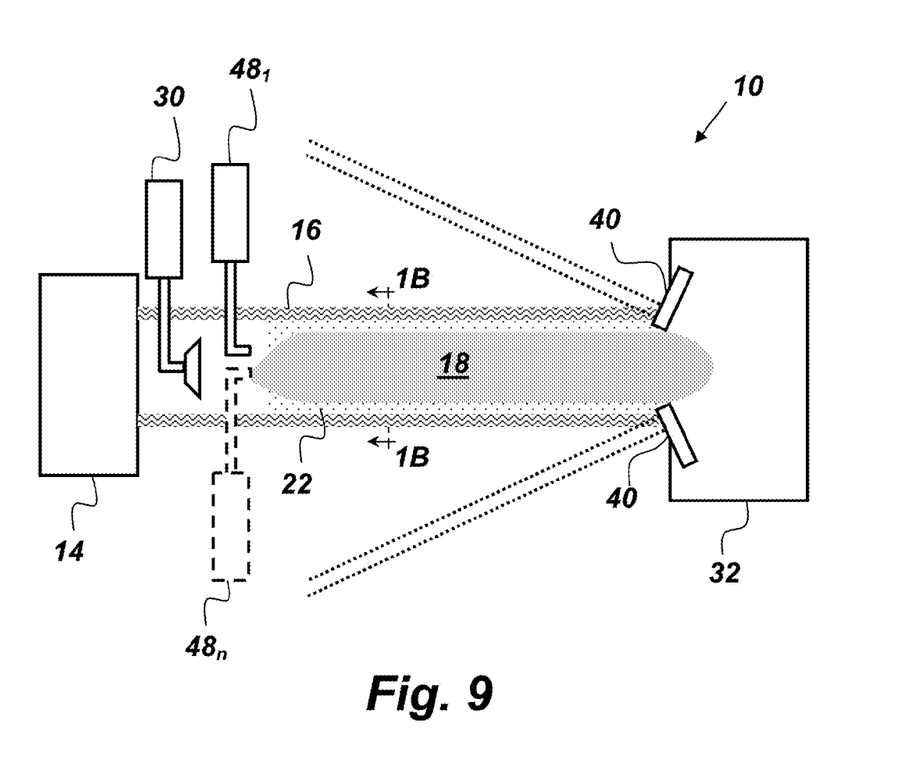
FIG. 9 is a side-view illustration of an embodiment of a fluid-channeling device.

FIG. 9 depicts an embodiment of the fluid-channeling device 10 that comprises multiple fluid injectors $48_1$ and $48_n$. Although only two fluid injectors 48 are shown in FIG. 9, it is to be understood that the fluid-channeling device may comprise any desired number of fluid injectors 48. Each fluid injector 48 may be connected to a different fluid source and is configured to inject a different type of fluid into the vortex 20 of the collimated vortex beam 16. The same collimated vortex beam 16 may be used to transport various different types of fluid without cross-contamination. The beam generator 14 may be operatively coupled to each of the fluid injectors 48 such that fluid from any one given fluid injector 48 may be introduced into the vortex 20 at a time. The beam generator 14 may be pulsed on and off for different fluid transport operations as a means of avoiding cross-contamination. The multiple injector embodiment may be used in conjunction with the multiplexer embodiment described above to provide a fluid-channeling device 10 that is capable of delivering a variety of different fluids to any given receiving channel 42.

The fluid-channeling device 10 may be used to mix two or more different fluids together. For example, a relatively dense liquid may transported by the collimated vortex beam 16 after being injected inside the vortex 20 where another, relatively-less-dense liquid is also injected. The relatively-less-dense liquid will be vaporized to create the pseudo wall 22 resulting in simultaneous mixing and transporting of the two fluids in the collimated vortex beam 16. The thickness of the pseudo wall 22 may be controlled by tuning the wavelength of the collimated vortex beam 16. The fluid-channeling device 10 may also be used as a fluidic incubating channel to incubate a deoxyribonucleic acid (DNA) sample mixed with a polymerase chain reaction (PCR) mixture for whole genome amplification (WGA) processes.

The fluid-channeling device 10 may be used in a nano/microfluidic environment for transporting fluid to/from various physical channels with at least one dimension less than 1 mm. The fluid 18 may be any of the fluids used in nano/microfluidic devices such as whole blood samples, bacterial cell suspensions, protein or antibody solutions and various buffers. The fluid-channeling device 10 may be integrated onto a substrate chip.

From the above description of the fluid-channeling device 10, it is manifest that various techniques may be used for implementing the concepts of the fluid-channeling device 10 without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the fluid-channeling device 10 is not limited to the particular embodiments described herein, but is capable of many embodiments without departing from the scope of the claims.

We claim:

1. A fluid-channeling device comprising:
   a fluid source; and
   a beam generator configured to generate a collimated vortex beam, wherein the beam generator is operatively coupled to the fluid source such that fluid from the fluid source may be introduced into a vortex of the collimated vortex beam, and wherein the collimated vortex beam is tuned such that when the fluid is in the vortex the fluid interacts with the collimated vortex beam to create an insulating pseudo-wall between the collimated vortex beam and the fluid such that the fluid is suspended in, and capable of traveling through, the vortex.

2. The device of claim 1, wherein the radiation pressure of the collimated vortex beam is greater than or equal to the vapor pressure of the fluid.

3. The device of claim 2, further comprising a fluid driver configured to cause fluid within the vortex to move through the vortex along a path of the collimated vortex beam.

4. The device of claim 3, further comprising a tubular enclosure configured to surround the vortex beam between the fluid driver and the fluid source without touching the vortex beam, wherein the fluid driver is a suction pump.

5. The device of claim 3, wherein the fluid driver is a gas pulse generator.

6. The device of claim 3, further comprising a fluid receiver optically aligned with the collimated vortex beam and configured to receive the fluid within the vortex, and wherein during transit between the fluid source and the fluid receiver, the fluid is supported by nothing but the collimated vortex beam.

7. The device of claim 6, further comprising a plurality of fluid sources, wherein the beam generator is operatively coupled to each of the fluid sources such that fluid from any one given fluid source may be introduced into the vortex at a time.

8. The device of claim 6, further comprising a plurality of fluid receivers, wherein the beam generator is pivotable and is operatively coupled to each of the fluid receivers such that the collimated vortex beam may be aimed at any one given fluid receiver at a time.

9. The device of claim 2, wherein the fluid is a gas.

10. The device of claim 2, wherein the fluid is a plasma.

11. The device of claim 2, wherein the fluid is a liquid.

12. The device of claim 11, wherein the temperature of the collimated vortex beam is greater than, or equal to, the Leidenfrost point of the fluid, such that the pseudo-wall is a layer of fluid vapor/gas created by the Leidenfrost effect.

13. A method for transporting a first fluid, comprising the following steps:

generating a first optical beam;

filtering the first optical beam to create a collimated vortex beam having a radiation pressure greater than or equal to a vapor pressure of the first fluid, and wherein the temperature of the collimated vortex beam is greater than, or equal to, the Leidenfrost point of the first fluid;

injecting the first fluid into the vortex of the collimated vortex beam such that the first fluid is suspended within the vortex due to the Leidenfrost effect by a layer of first fluid vapor/gas; and driving the first fluid through the vortex along the path of the collimated vortex beam by pumping a pulse of gas along the propagation path of the collimated vortex beam.

14. The method of claim 13, further comprising mixing a second fluid with the first fluid by transporting the first and second fluids together through the vortex.

15. The method of claim 13, further comprising controlling a thickness of the first fluid vapor by tuning the wavelength of the collimated vortex beam.

16. The method of claim 13, wherein the first fluid is a mixture of deoxyribonucleic acid (DNA) and a polymerase chain reaction (PCR) mixture.

17. A microfluidic-channeling device comprising:
    a beam generator configured to output a first optical beam;
    a filter configured to transform the first optical beam into a collimated vortex beam;
    a fluid injector configured to inject a fluid into the vortex of the collimated vortex beam, wherein the temperature of the collimated vortex beam is greater than, or equal to, the Leidenfrost point of the fluid, and wherein the collimated vortex beam has a radiation pressure greater than or equal to a vapor pressure of the fluid, such that the fluid is held within, and is capable of moving through, the vortex due to the Leidenfrost effect; and
    a fluid receiver optically aligned with the collimated vortex beam and configured to receive the fluid from the vortex.

18. The device of claim 17, further comprising a fluid driver configured to cause the fluid when it is within the vortex to move through the vortex along a path of the collimated vortex beam.

19. The device of claim 18, further comprising a plurality of fluid receivers, wherein the beam generator is adjustable and is operatively coupled to each of the fluid receivers such that the collimated vortex beam may be aimed at any one given fluid receiver at a time.

20. The device of claim 19, wherein during transit between the injector and the receiver, the fluid is supported by nothing but the collimated vortex beam.

* * * * *